(12) United States Patent
Enggaard

(10) Patent No.: US 6,899,699 B2
(45) Date of Patent: May 31, 2005

(54) AUTOMATIC INJECTION DEVICE WITH RESET FEATURE

(75) Inventor: Christian Enggaard, Hillerød (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/038,781

(22) Filed: Jan. 2, 2002

(65) Prior Publication Data

US 2002/0120235 A1 Aug. 29, 2002

Related U.S. Application Data

(60) Provisional application No. 60/260,602, filed on Jan. 9, 2001.

(30) Foreign Application Priority Data

Jan. 5, 2001 (DK) .......................... 2001 00018

(51) Int. Cl.⁷ ............................... A61M 5/00
(52) U.S. Cl. .................. 604/246; 604/207; 604/208; 604/211
(58) Field of Search ............... 604/246, 207, 604/208, 209, 210, 211, 218, 223, 224, 232, 235, 181, 187, 192, 219, 220

(56) References Cited

U.S. PATENT DOCUMENTS 5,104,380 A * 4/1992 Holman et al. ............. 604/117
5,626,566 A * 5/1997 Petersen et al. ............ 604/208
5,827,232 A * 10/1998 Chanoch et al. ........... 604/208

* cited by examiner

*Primary Examiner*—Christopher L. Chin
*Assistant Examiner*—Ann Y Lam
(74) *Attorney, Agent, or Firm*—Marc A. Began, Esq.; Richard W. Bork, Esq.; Reza Green, Esq.

(57) ABSTRACT

The present invention relates to a dose setting and expelling device comprising a drive member and a dose setting mechanism which simultaneously sets a given dose and stores the energy necessary for a subsequently driving the drive member in order to expel a dose of medicine from an injection device. According to the invention the dose setting mechanism allows adjustment in both directions, such that a given set dose can be reduced or cancelled by reversing the input motion, typically by rotating a setting member backwardly, this in contrast to the known devices which either requires an additional release mechanism or which cannot be reversed at all.

23 Claims, 7 Drawing Sheets

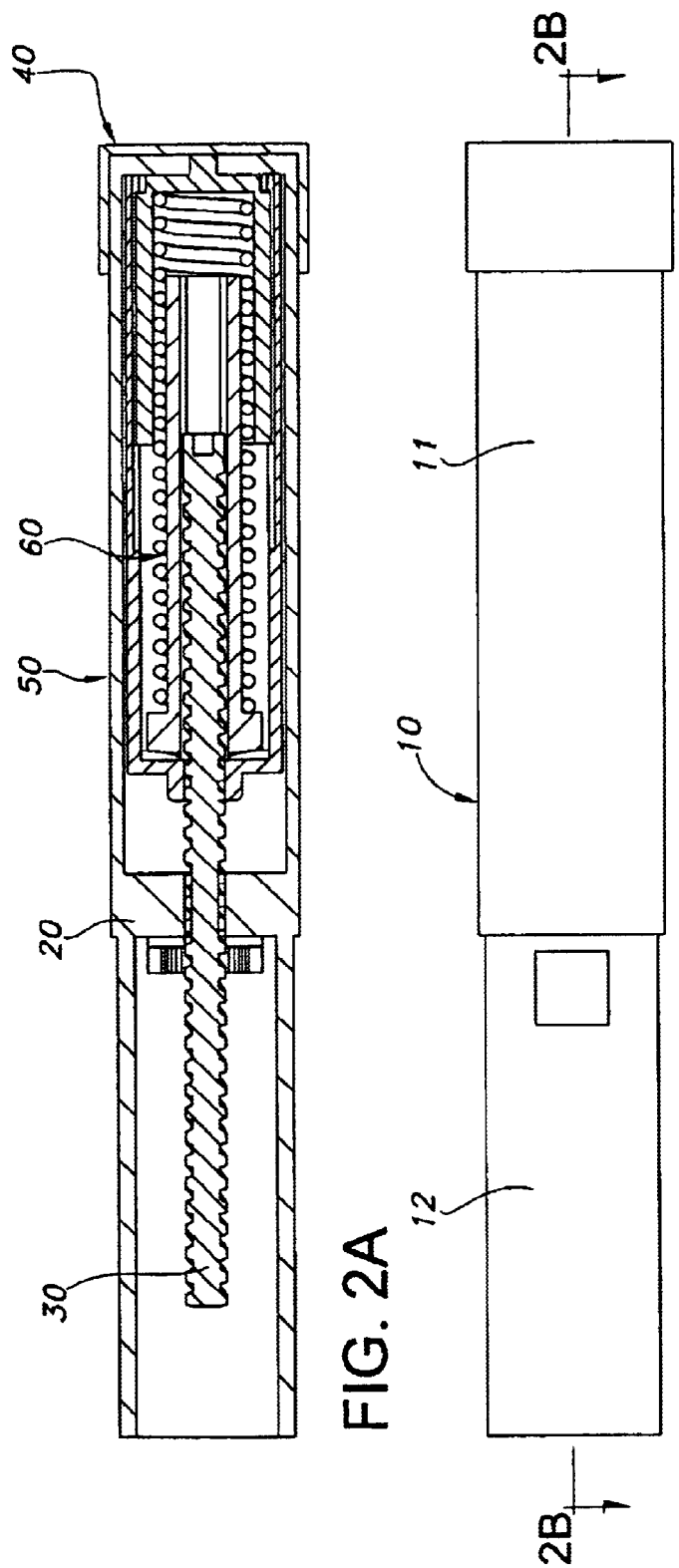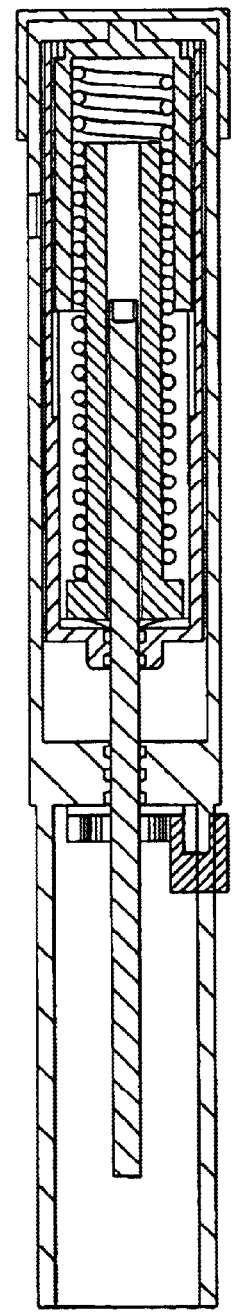
FIG. 2A
FIG. 2B

AUTOMATIC INJECTION DEVICE WITH RESET FEATURE

This application claims benefit of 60/260,602, filed on Jan. 9, 2001.

The present invention relates in general to a dose setting and expelling device for use in conjunction with an injection device comprising a reservoir containing a fluid. In a more narrow aspect the present invention relates to a portable apparatus comprising such a dose setting and expelling device and adapted to accommodate a drug-containing ampoule or cartridge. In an even more narrow aspect the present invention relates to a pocket-size injection device for repetitive subcutaneous injection of individually set doses of a drug from a reservoir placed in the device. The injection device may be in the form of a pen shaped syringe device, the cartridge being replaceable or integrally formed with the device.

BACKGROUND OF THE INVENTION

Injection devices, typically in the form of pen shaped syringes, are especially used by diabetics who have to inject themselves frequently with an insulin preparation to keep their blood glucose level within tolerable limits. However, recently different kinds of medicine, for example growth hormone, have been administered in the same fashion.

The doses are mainly set by rotating, or dialling, part of the pen syringe relatively to the rest of the syringe and numbers forming a scale on the rotatable part of the syringe are moved in relation to an indicating mark on the rest of the syringe to indicate the set dose. When the user sets the dose, the syringe is actuated in order to express the dose of medicine. The actuation is normally provided by the user pressing some kind of button by a single movement up to a stop. This makes the injection stage independent of any need to assess what dose is being injected.

The injection device should be as simple as possible to use, i.e. the normal use should only imply setting a dose and injecting the set dose, and both these steps should be simple to perform and this condition is met by most prior-art pen devices.

However, for some users the actual step of expression the dose causes anxiety and a device which automatically expressed the dose on demand would be desirable. Such a facility also could provide for a more repeatable and smooth injection of the fluid. According to U.S. Pat. No. 5,104,380 this has been achieved by a syringe device comprising a body and a rotatable dose setting device mounted on the body and capable of being moved to a selected set position, a latch arranged to retain the setting device in the set position, and means arranged to release the latch to cause the set dose to be expelled. Movement of the dose setting device to the selected set position is accompanied by rotational straining of a spring, which, when the latch is released, provides the force for expelling the set dose. When the latch is released, the setting device is returned to an original position to drive a plunger through a one-way clutch to expel the set dose. The disclosed driving means comprises a quick pitch screw thread arrangement for transforming rotation of the setting device into linear movement of the plunger. The body is adapted for receiving a cartridge containing a fluid to be injected by having a cartridge container removable from the body for insertion of a cartridge and then removal of the cartridge container is arranged to release the quick pitch screw thread device thus allowing the plunger to be returned to an initial position.

However, not all pen syringes offer the opportunity to cancel a set dose, so if a dose once set is not wanted for injection the only way to bring the syringe back in its neutral position is to spill the dose. With syringes by which large doses may be set or in case the medicine is very expensive, as is the case with growth hormone, this is not acceptable.

In order to solve this problem U.S. Pat. No. 5,626,566 discloses a pen shaped syringe for repetitive injection of individually set doses of a medicine from a cylinder ampoule reservoir, comprising a dose setting member which allow a dose set to be cancelled by incorporating means provided to release a unidirectional coupling between a piston drive member and the dosing member. However, this design both requires a release mechanism to be actuated when a dose is to be reset as well as a manual actuating mechanism when the medicine is to be expressed.

SUMMARY OF THE INVENTION

It is thus an object of the present invention to provide a dose setting mechanism which solves one or more of the above identified problems.

According to a first aspect of the invention, this is provided by a dose setting device for an injection device (or apparatus), comprising a drive member and a dose setting mechanism which simultaneously sets a given dose and stores the energy necessary for a subsequently driving the drive member in order to expel a dose of medicine from the injection device, and where the dose setting mechanism allows adjustment in both directions, i.e. a given set dose can be reduced or cancelled by reversing the input motion, typically by rotating a setting member backwardly, this in contrast to the known devices which either requires an additional release mechanism or which cannot be reversed at all.

In a preferred embodiment, the invention provides a device for repetitive injection of individually set doses of a fluid or drug from a reservoir, comprising: a housing, a reservoir containing a fluid to be expelled, a drive member adapted to expel a dose of fluid from the reservoir, a spring means, a dose setting assembly mounted in the housing and connected to the spring means, the dose setting assembly comprising a member being moveable in a first direction to a selected set position against the spring means, wherein movement of the dose setting member is accompanied by straining of the spring, and wherein the dose setting device is moveable in a second direction to selectively adjust the set dose, a latch means associated with the housing to retain the injection device in the set position against the bias of the spring means, and the latch means being releasable to cause the drive member to expel the set dose from the reservoir, the force for expelling the set dose being provided by the spring means. Preferably the injection device is adapted to receive a reservoir in the form of a replaceable cartridge.

In a preferred embodiment the housing comprises an internal thread, the drive member being a longitudinal piston drive member (also termed drive member or plunger) having an external thread corresponding to the internal thread, the two threads having a pitch angle exceeding the friction angle therebetween. Thereby the driving movement (i.e. the forward movement of the piston drive member) can be obtained by simply pressing the piston drive member axially forwardly a given distance determined by the set dose, this resulting in a rotative movement of the drive member in the dosing direction. Such a thread is also known as non-locking.

In a further preferred embodiment the dose setting device comprises a coupling member in displaceable engagement with the dose setting member, the spring means acting on the coupling member which in turn acts on the dose setting member. Preferably, the dose setting member has an internal thread, the dose setting member being rotationally mounted on the drive member, and the coupling member arranged in sliding, non-rotational engagement with the piston drive member, the spring means acting on the coupling member in a direction corresponding to a longitudinal axis of the drive member; the dose setting member and the coupling member comprise mutually cooperating surfaces such that rotation of the dose setting member in order to set a dose results in straining of the spring means as the coupling member is driven backwardly.

Preferably the thread between the dose setting member and the piston drive member is of the non-locking type, however this necessitates a coupling or "brake" between the dose setting member and the coupling member as otherwise the spring means would automatically be allowed to expand thus driving the dose setting member backwardly to its initial position. However, according to the stated object of the invention, the coupling should allow the dose setting member to be rotated backwards in order to selectively adjust the set dose.

In other words, the coupling between the dose setting member and the coupling member should allow the dose setting member to be rotated in either direction, yet preventing the spring means to counter rotate the dose setting member. This object can be achieved by providing a coupling between the above-described cooperating surfaces of the dose setting member and the coupling member, the coupling providing a resistance against rotation which is sufficiently to prevent the spring means to counter rotate the dose setting member, the resistance being easily overcome by a user rotating the dose setting member in either direction. In this way the user can "dial up" and "dial down".

In preferred embodiments a bi-directional coupling between the dose setting member and the coupling member is provided by coupling parts having circular surfaces provided with sector shaped teeth having ramp shaped edges, the surfaces being forced against each other with the ramp shaped edges of the teeth on one surface abutting the ramp shaped edges of the teeth on the other surface. When the dose setting member is rotated in either the dose setting or adjusting direction, the teeth on the coupling parts will slide with their ramp shaped parts over each other, whereby the dosing member is axially displaced against the force of the spring and will jump back each time a top of the teeth is reached. Each jump back may be heard and/or sensed by the operator, and the pitch of the toothing may be chosen so that a jump back takes place each time the dose setting is increased by say one unit.

In a further preferred embodiment the coupling is a frictional coupling provided between cooperating surfaces, the necessary compression force between the two surfaces being provided by the spring means acting on the coupling member. The two coupling surfaces could be provided by any suitable combination of materials and surface configurations providing the necessary friction.

If a more simple construction is desirable, the above described arrangement with a coupling member can be dispensed with. Therefore, in a further preferred embodiment the dose setting device comprises a dose setting member having an internal thread, the dose setting member being rotationally but frictionally mounted on the drive member, the friction between the dose setting member and the drive providing a resistance against rotation which is sufficiently to prevent the spring means to counter rotate the dose setting member, however, the resistance being easily overcome by a user rotating the dose setting member in either direction.

In order to provide an indication of the set dose, the dose setting member may comprise a sleeve with numbers printed along a helical line which can be inspected through an opening, or window, in the housing of the device, the opening allowing only a portion, preferably on-only one, of the numbers on the sleeve. When the sleeve is rotated and simultaneously axially displaced along with the opening a number indicating the actually set dose can be inspected through opening.

In a preferred embodiment the non-rotational engagement between the coupling member and the drive member is established by a non-circular opening in the coupling member through which the correspondingly non-circular drive member slides, for example provided by opposed flattened surfaces.

In a further preferred embodiment, a setting member is provided which can be rotated without any axial movement, the rotation being transferred to the dose setting member, this allowing a dose setting device of constant length. The setting member could be in the form of a knob, a ring or a skirt.

According to a second aspect of the invention, there is provided a dose setting device for an injection device, comprising a drive member and a dose setting mechanism which simultaneously sets a given dose and stores the energy necessary for a subsequently driving the drive member in order to expel a dose of medicine from the injection device, and where the dose setting mechanism can be released resulting in a re-setting of the dose, i.e. to the initial "0" position, after which the dose can be set again. Such a type of resetting arrangement could advantageously be used with a device of the type known from U.S. Pat. No. 5,104,380.

When used as part of an injection device, the injection device typically comprises a compartment into which a fluid containing reservoir can be inserted and locked in position, the reservoir comprising a relatively small opening at a foremost end (where typically an injection needle is arranged to provide communication with the interior of the reservoir, the reservoir being supplied in a sealed condition) and a rearmost end closed by a piston in sliding engagement with an internal surface of the reservoir, a medicament being enclosed between the opening and the piston, the dose setting and expelling device of the present invention being arranged such that the piston drive member can be brought into contact with the piston, this resulting in a dose of fluid or drug being expelled as the drive member is moved forwardly by the spring means action. Indeed, in order to properly set a desired dose, the dose setting device and the cross-sectional area of the piston have to be adapted to each other.

In a further aspect of the present invention, a method for infusing a flowable drug into a living subject is provided, comprising the steps of providing an injection device for repetitive injection of individually set doses of a fluid (or drug) from a reservoir, the injection device comprising a housing, a reservoir containing a fluid to be injected and having an outlet means therefore, a drive member adapted to expel a dose of medicine from the reservoir, a spring means, a dose setting assembly mounted in the housing and connected to the spring means, the dose setting assembly comprising a dose setting member being moveable in a first direction to a selected set position against the bias of the spring means, wherein movement of the dose setting member is accompanied by straining of the spring, and wherein the dose setting member is moveable in a second direction to selectively adjust the set dose, a latch means associated with the housing to retain the device in the set position against the bias of the spring means, and the latch means being releasable to cause the drive member to expel the set dose from the reservoir, the force for expelling the set dose being provided by the spring means, the method comprising the further steps of establishing a flow connection between the outlet means and the subject, selecting a dose by operating the dose setting member, and releasing the latch means to cause the drive member to expel the set dose from the reservoir. In preferred embodiments of the method, an infusion device as described herein is used.

As used herein, the term "drug" is meant to encompass any drug-containing flowable medicament capable of being passed through a delivery means such as a hollow needle in a controlled manner, such as a liquid, solution, gel or fine suspension. There is essentially no limitation on the type of liquid drug which can be used with the invention other than to exclude those liquid drugs which would be inappropriate to deliver to the subject in a fashion using the injection device of the invention. Representative drugs include peptides, proteins, and hormones. In the description, the preferred embodiments will be suitable for use with insulin. Correspondingly, the term "subcutaneous" infusion is meant to encompass any method of infusion into a subject.

BRIEF DESCRIPTION OF THE DRAWINGS

In the following the invention will be further described with references to the drawings, wherein FIG. 1 shows an external view of a pen-shaped syringe comprising a dosing and expelling device according to a first embodiment of the invention, and in a mode before dialling a dose, FIG. 2 shows an external view of the pen-shaped syringe of FIG. 1 in a mode of dialling a dose (which is not apparent from the outside in this representation), FIG. 2A shows a cross section through the syringe in FIG. 2 corresponding to the plane of the paper, FIG. 2B shows a cross section through the syringe in FIG. 2 along the line B—B, FIG. 3 shows an external view of the pen-shaped syringe of FIG. 1 in a mode after injecting a dose (which is not apparent from the outside in this representation)

DESCRIPTION OF THE PREFERRED EMBODIMENTS

Figure 1A:
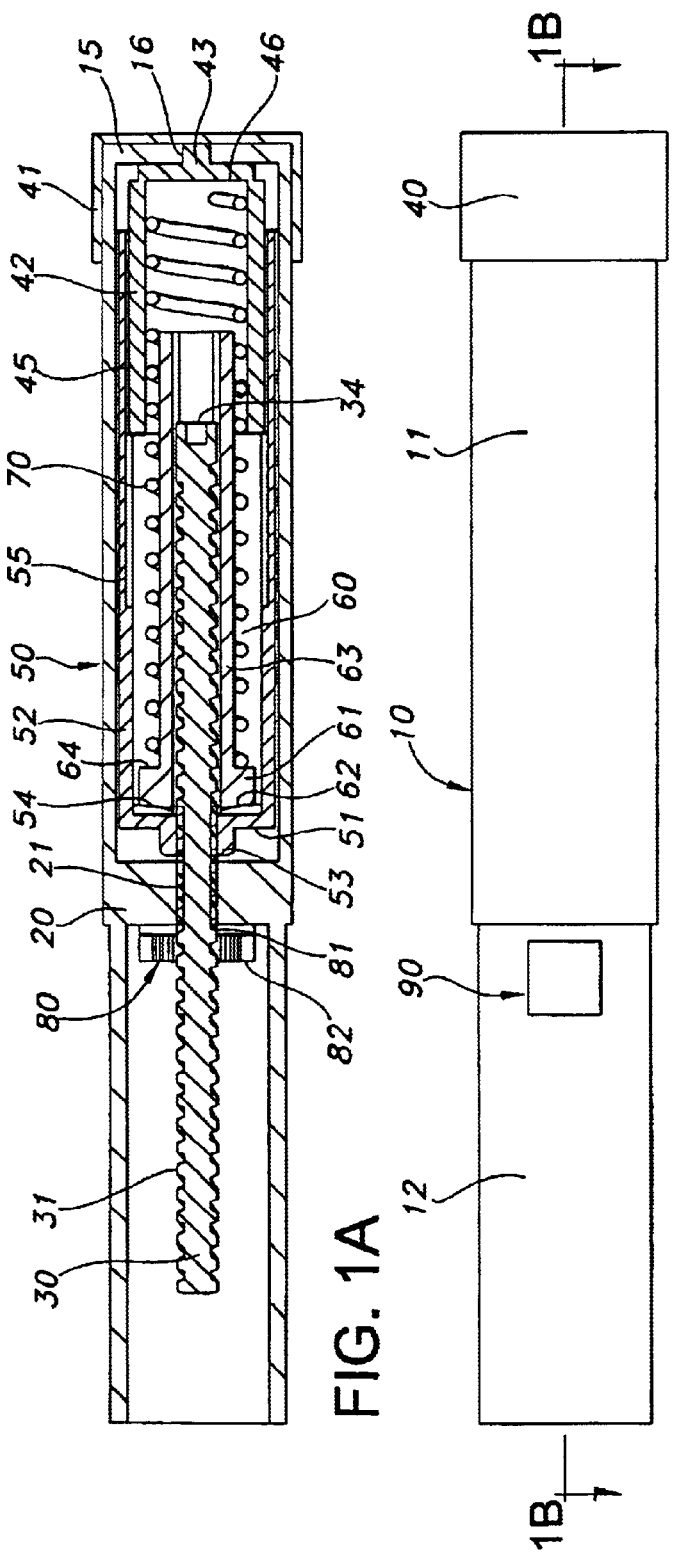
FIG. 1A shows a cross section through the syringe in FIG. 1 corresponding to the plane of the paper.

In the following the orientation of the different elements are described with help of the terms front and rear, respectively forwards and rearwards, denoting orientations toward left and right, respectively, in the figures. The term longitudinal is used with reference to the general longitudinal orientation of the shown syringe.

The syringe shown in FIG. 1 as seen from the outside comprises a longitudinal housing 10 with a first (rear) portion 11 and a second (front) portion 12, the first portion comprising a first compartment with the dose setting device of the present invention and the second portion comprising a second compartment adapted to accommodate a medicine-containing ampoule or cartridge. In the shown embodiment the second portion is formed integrally with the first portion, however, the second portion is not part of the present invention and could, correspondingly, also be provided as a separate element which could be connected to the first portion by, for example, a threaded or bayonet connection. When removing the first portion, an empty cartridge (not shown) can be removed, the plunger (to be described below) can be returned to its initial position, and a new cartridge can be inserted where after the portions again can be connected to each other. In case the two portions are formed integrally, the foremost end of the first portion should be closed by an additional element (not shown) in order to provide a compartment for the ampoule.

The syringe further comprises a latch or trigger member 90 and a dose setting knob 40 arranged at the rear end of the syringe.

As shown in FIG. 1A a partition member 20 is arranged between the first and second portions, the partition member having an opening with an internal thread 21, the partition thereby serving as a nut member, however, the term nut does not imply that the thread has to be defined by a bore but could also be defined between two opposed members. A longitudinal plunger 30 serving as a piston drive member (i.e. when the plunger is positioned with its foremost end against a piston in the ampoule) is arranged through the opening, the plunger having an external thread 31 corresponding to the internal thread of the partition allowing the plunger to be threaded through the opening. The thread of the plunger/nut connection has a pitch angle exceeding the friction angle of the nut and plunger. Thereby forward movement of the plunger can be obtained by simply pressing the plunger axially forwardly, this resulting in a rotative movement of the drive member in the forwards direction. Such a thread is also known as non-locking. The plunger further comprises two opposed and parallelly arranged, planar side surfaces 32, 33 providing a "partial" external thread, however, this has no functional influence on the thread connection as such. The purpose of the opposed surfaces will be apparent from the below.

The dose setting knob 40 comprises an outer cap portion 41 to be gripped by a user and an inner forwardly projecting cup-like skirt portion 42, the two portions being connected by a shaft 43 arranged through an opening 16 in the rear end wall 15 of the housing, whereby the knob is allowed to rotate but not to be axially displaced relative to the housing.

Figure 4:
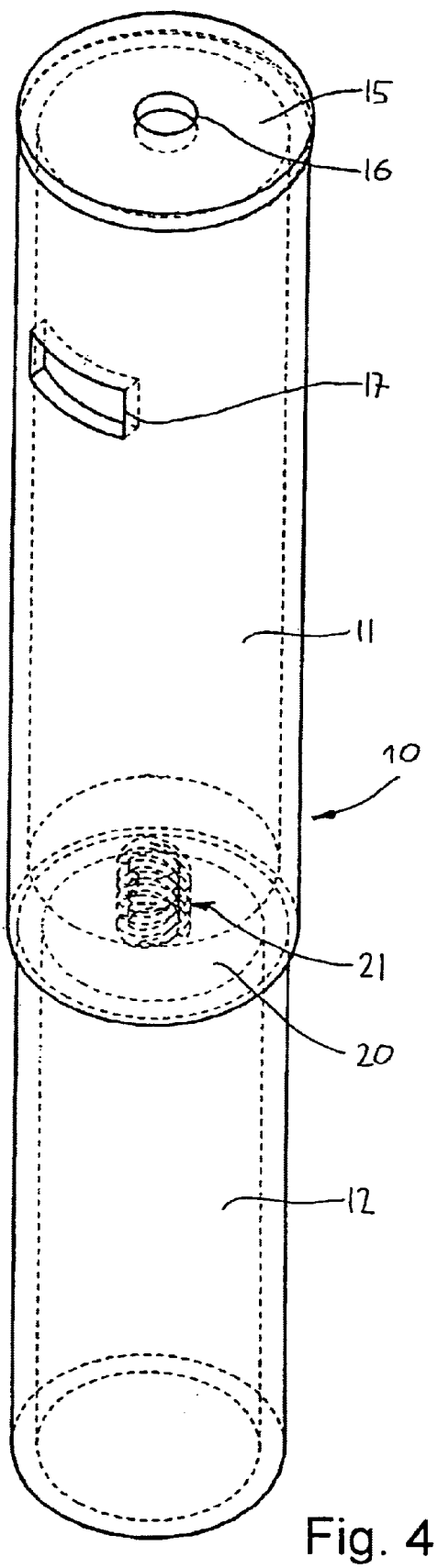
FIG. 4 shows a housing member.

The dose setting member 50 comprises a foremost end wall 51 and a rearwardly arranged skirt portion 52. The end wall has an opening with an internal thread 53, the end wall thereby serving as a second nut member through which the plunger 30 is arranged. The thread 53 corresponds to the internal thread 21 thus allowing non-locking rotation of the plunger. The end wall further comprises a rearwardly facing coupling surface 54 to be described below. The skirt portion 52 of the dose setting member comprises longitudinal grooves 55 on its inner surface engaging corresponding longitudinal tongue members 45 on the outer surface of the skirt portion 42 of the knob 40, whereby the two skirt members are allowed to slide axially but not to rotate relative to each other. Indeed, any suitable configuration could be used to provide this functional relation between the two skirt members. Numbers (not shown) are printed along a helical line on the external surface of the skirt 52 which can be inspected through a window 17 (see FIG. 4) in the housing of the device, the window allowing only a portion, preferably only one, of the numbers on the sleeve to be inspected.

The tubular coupling member 60 comprises a foremost extension 61 with a forwardly facing coupling surface 62, as well as a rearwardly oriented tubular skirt portion 63. The skirt portion and the extension is formed with two internal, opposed and parallelly arranged, planar surfaces 68, 69 (see FIG. 7) corresponding to the opposed surfaces 32, 33 on the plunger, whereby the coupling member and the plunger are allowed to slide axially but not to rotate relative to each other. Indeed, any suitable configuration could be used to provide this functional relationship between the plunger and coupling member.

A helical spring 70 is supported at its respective ends at an rearwardly facing surface 64 of the extension 61 and at an inner end surface 46 of the knob skirt, the spring thus providing a biasing force on the coupling member. The shown spring may be replaced by any suitable element which can store and release energy, for example a gas-filled member or a foam body, such structures being examples of spring means.

The above-described coupling surfaces 54, 62 on the dose setting member and the coupling member co-operate to provide a bi-directional coupling between the dose setting member and the coupling member. In the shown embodiment the coupling is provided by coupling parts having circular surfaces provided with sector shaped teeth 57, 67 (see FIGS. 5 and 7 respectively) having ramp shaped edges, the surfaces being forced against each other by the spring 70 with the ramp shaped edges of the teeth on one surface abutting the ramp shaped edges of the teeth on the other surface. When the dose setting member is rotated in either a dose setting or an adjusting direction, the teeth on the coupling parts will slide with their ramp shaped parts over each other, whereby the dose setting member is axially displaced relative to the plunger (due to the threaded connection) against the force of the spring and will jump back each time a top of the teeth is reached. Each jump back may be heard and sensed by the operator, and the pitch of the toothing may be chosen so that a jump back takes place each time the dose setting is increased by say one unit.

A locking member 80 is provided on the plunger in order to prevent the plunger from rotating during the setting operation, i.e. during the rotation of the dose setting member on the plunger. The locking member is in the form of a wheel-like member comprising an opening 81 having opposed and parallelly arranged, planar surfaces 83, 84 (see FIG. 9) corresponding to the opposed surfaces 32, 33 on the plunger, whereby the tubular portion and the plunger are allowed to slide axially but not to rotate relative to each other. The locking member is arranged such that it is allowed to rotate but not move axially with with respect to the housing. The locking member further comprises a forwardly projecting, circumferential skirt with a plurality of axially aligned detents 82.

A latch member 90 comprising an inner latch arm 91 is arranged in the housing wall, the latch member being moveable between a setting position in which the latch arm engages between the detents on the locking member thereby preventing the locking member and thus the plunger from rotating, and a dosing position in which the latch arm disengages the detents on the locking member thereby allowing the locking member and thus the plunger to rotate. Preferably the latch member is biased towards its setting position.

Figure 1B:
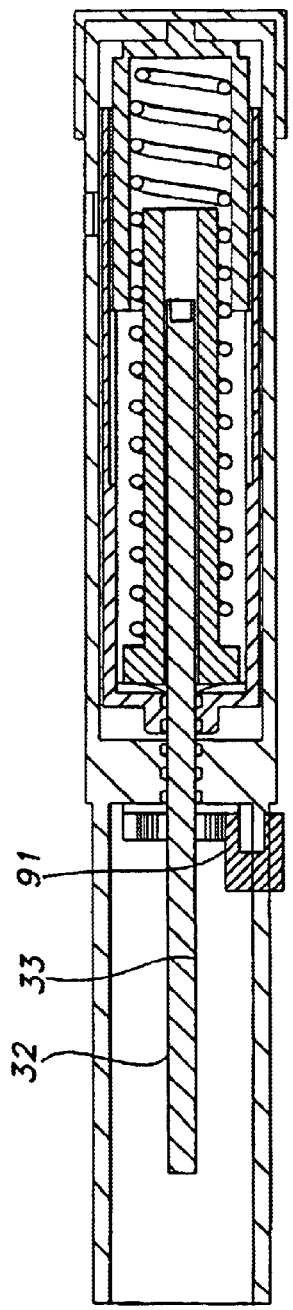
FIG. 1B shows a cross section through the syringe in FIG. 1 along the line B—B.

Next operation of the dose setting and expelling device of the present invention will be described with reference to the figures. When a fresh medicine-containing ampoule equipped with a fine needle (neither shown) is loaded into the syringe device, the piston in the ampoule is in its rearmost position and the plunger is positioned with its foremost end against the piston. During use of the syringe the plunger moves the piston forwards thereby expelling the medicine. FIGS. 1A and 1B show an intermediate position in which the plunger has been advanced approximately half the full stroke length and with the dose setting member in its "initial" position with a "0" showing in the window.

When setting a dose, the user preferably grips the housing with one hand, using the other hand to select (i.e. dial up) a desirable dose by rotating the dose setting knob 40. Due to the groove and tongue arrangement 45, 55 the dose setting member is rotated and threaded rearwardly relative to the plunger. During dose setting the user can control the setting by inspecting the numbers printed on the dose setting member as they pass the window, the numbers being indicative of the length the dose setting member has been rotated rearwards, and thus indicative of the subsequent stroke length for the plunger. If the dose is set too high, the user can simple adjust (i.e. dial down) the dose by turning the knob in the opposite direction until the number corresponding to the desired dose size shows up in the window.

As the dose setting member is rotated in either a dose setting or an adjusting direction, the teeth on the coupling parts will slide with their ramp shaped parts over each other, whereby the dose setting member is axially displaced relative to the plunger (due to the threaded connection) against the force of the spring and will jump back each time a top of the teeth is reached. As the coupling member is moved rearwardly the spring is compressed thus storing energy for the subsequent dosing. This situation is illustrated in FIGS. 2A and 2B.

When the desired dose is set the user advances the needle through the skin and the syringe is ready to expel the set dose which is performed when the user depresses the latch member thus releasing the locking member 80 and thus the plunger which can now rotate freely.

Figure 3A:
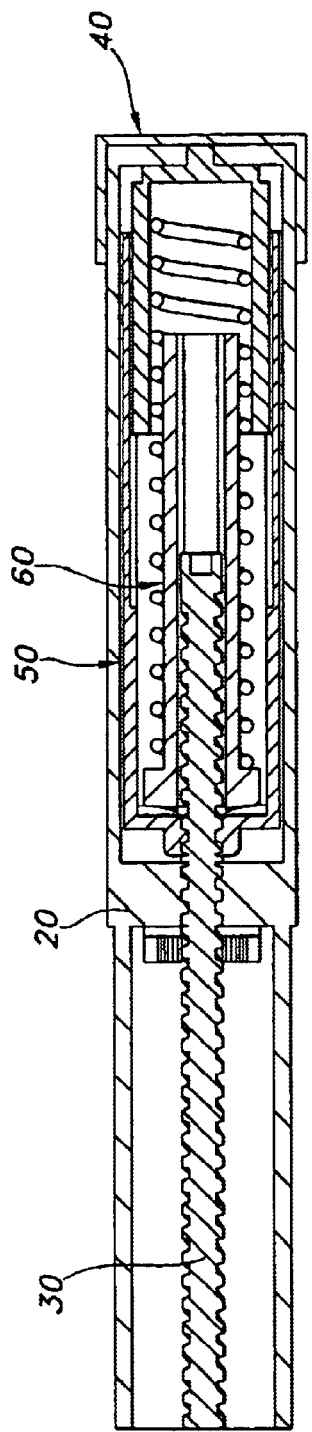
FIG. 3A shows a cross section through the syringe in FIG. 3 corresponding to the plane of the paper.
Figure 3B:
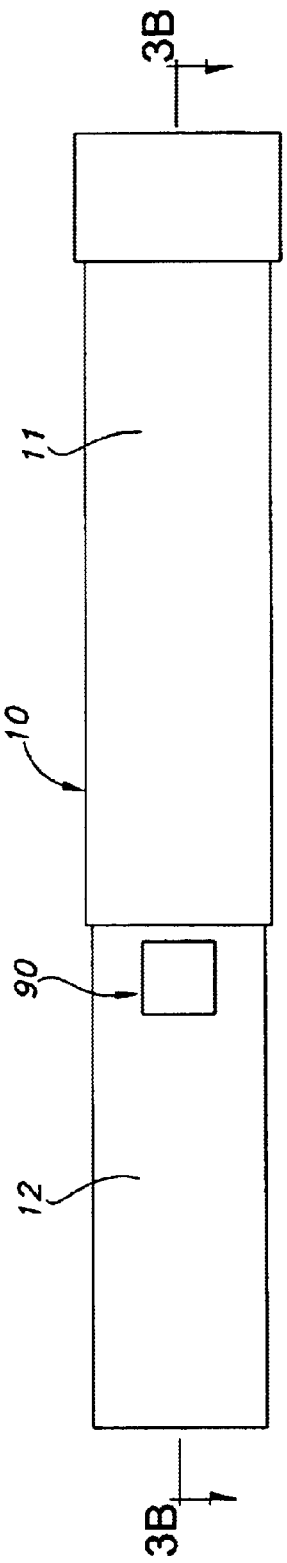
FIG. 3B shows a cross section through the syringe in FIG. 3 along the line B—B.

The axial force exerted by the spring 70 is transmitted to the plunger through the coupling member 60 and the dose setting member 50 (corresponding to the threaded connection) this resulting in a rotational forward movement of the plunger due to the non-locking thread connection between the plunger and the internal thread 21. As the coupling member cannot rotate relative to the rotating plunger, the dose setting member also rotates together with the plunger, this bringing the dose setting member back to its initial rotational position with a "0" showing in the window. This situation is illustrated in FIGS. 3A and 3B.

An "end of content" function (i.e. for the ampoule) is provided by the dose setting member simply abutting the rearmost portion 34 of the plunger as the threaded portion ends. The maximum possible dose is set when the rearmost end of the dose setting member abuts the rear end of the housing. The dose setting member is prevented from rotating past its "0" position as it abuts the partition wall.

The above-described device can either be provided for single use or for re-use in which case the dose setting mechanism will have to be reset, i.e. the plunger moved backwardly, in order to allow a new cartridge to be inserted into the syringe. The plunger is moved backwardly simply by rotating the plunger, however, as the plunger is normally positioned inside a front portion 12 of the housing, the front portion should either be removed in order to allow a user to properly grip the plunger, or the plunger should be rotated indirectly. The latter could be achieved by providing a housing having releasable front and rear portions 11, 12 (not shown) in order to allow the portions to be rotated relative to each other. As the front housing is rotated relative to the rear housing and the dose setting member, the latched locking member 80, in sliding non-rotational engagement with the plunger, provides rotation of the plunger 30 which is then treaded rearwardly through the internal threads 21, 53 of the partition member 20 respectively the dose setting member. In order to prevent the dose setting member from rotating, the knob 40 should be gripped together with the rear housing in order to prevent relative rotation between these members. As the coupling member 60 is in sliding non-rotational engagement with the plunger, it is correspondingly rotated resulting in a "clicking" relative rotation between the two mutually cooperating coupling surfaces 54, 62. When the plunger is brought to its rearmost position, the front and rear portions are again locked to each other and the syringe is ready to be loaded with a new cartridge.

Figure 5:
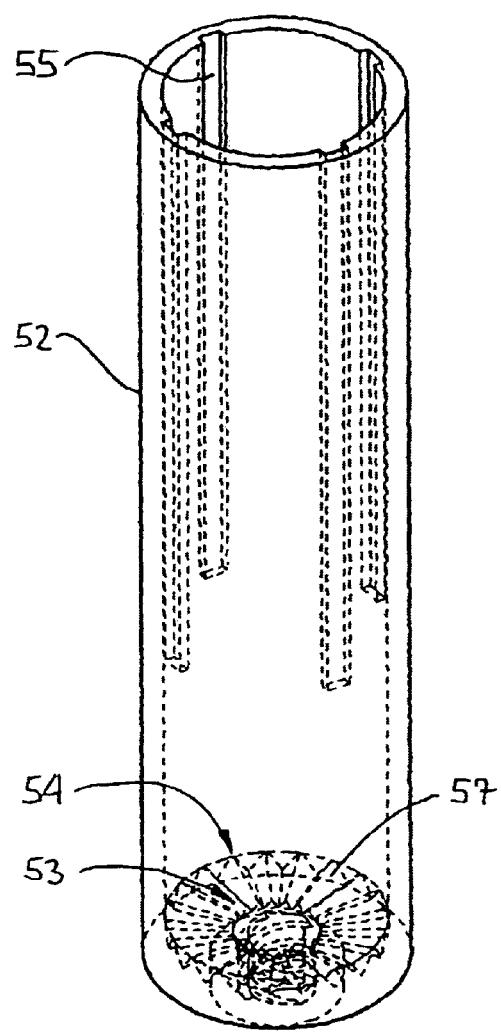
FIG. 5 shows a dose setting member.
Figure 6:
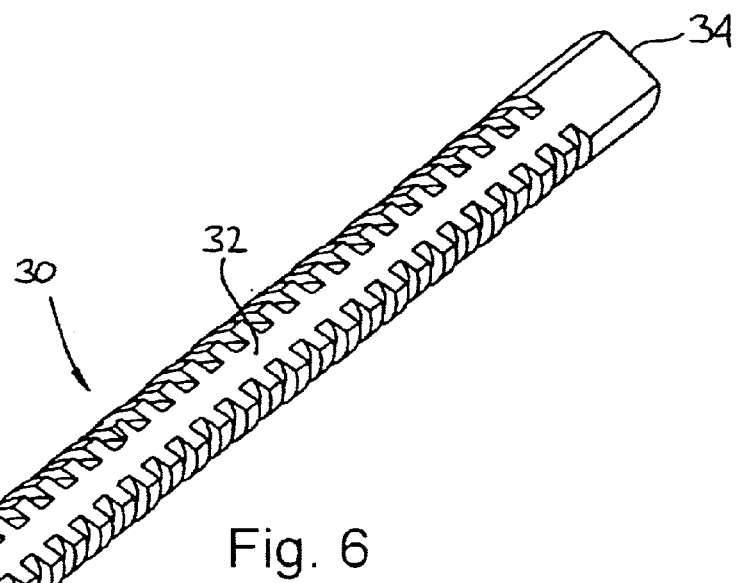
FIG. 6 shows a piston drive member.
Figure 7:
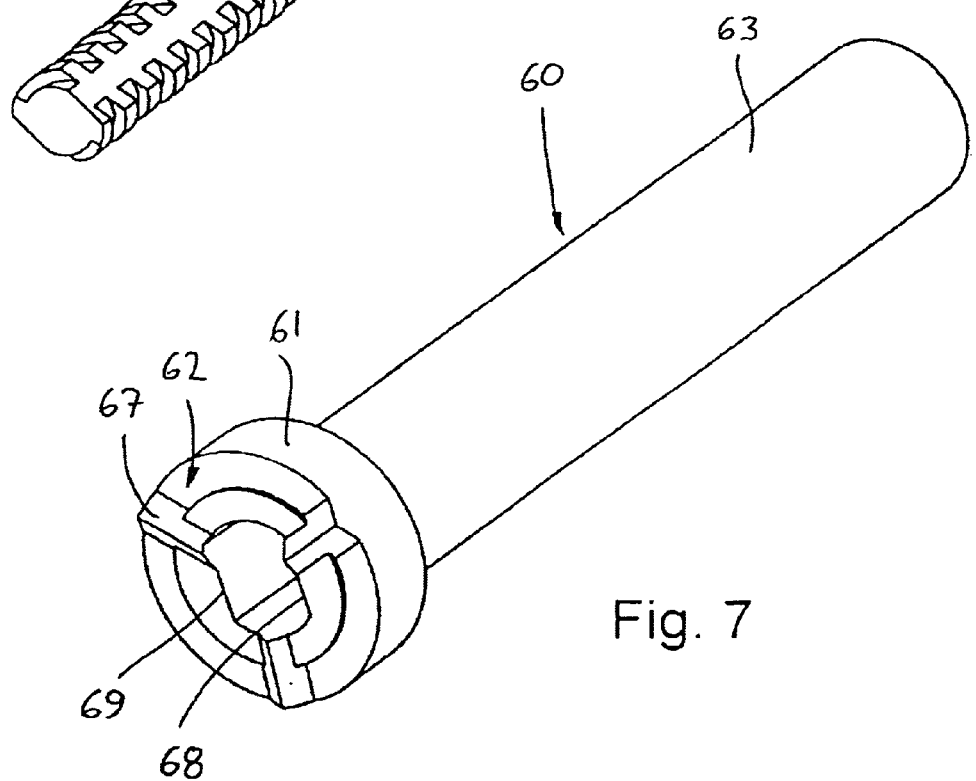
FIG. 7 shows a coupling member.
Figure 8:
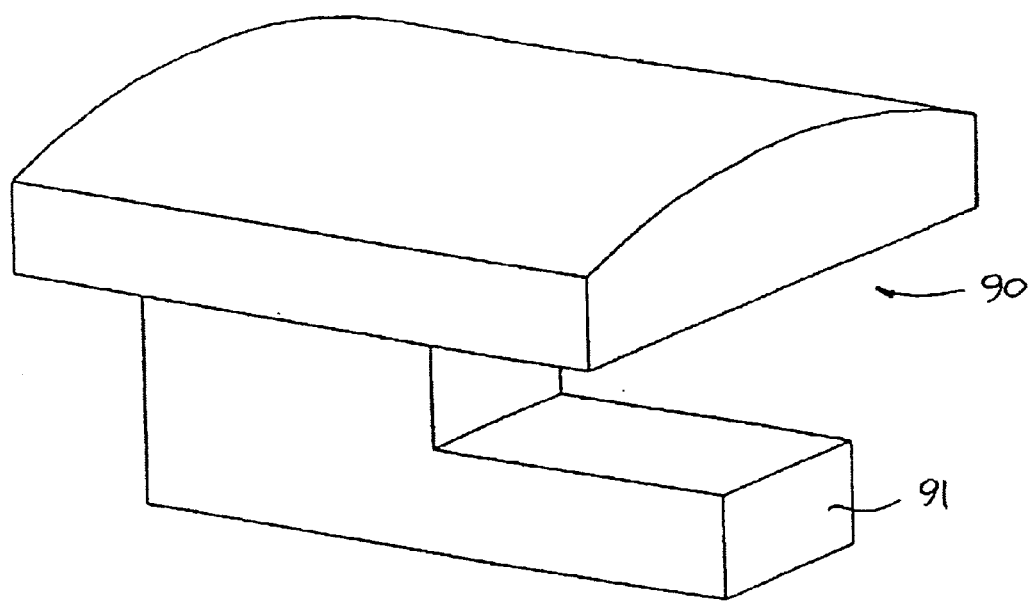
FIG. 8 shows a latch member.
Figure 9:
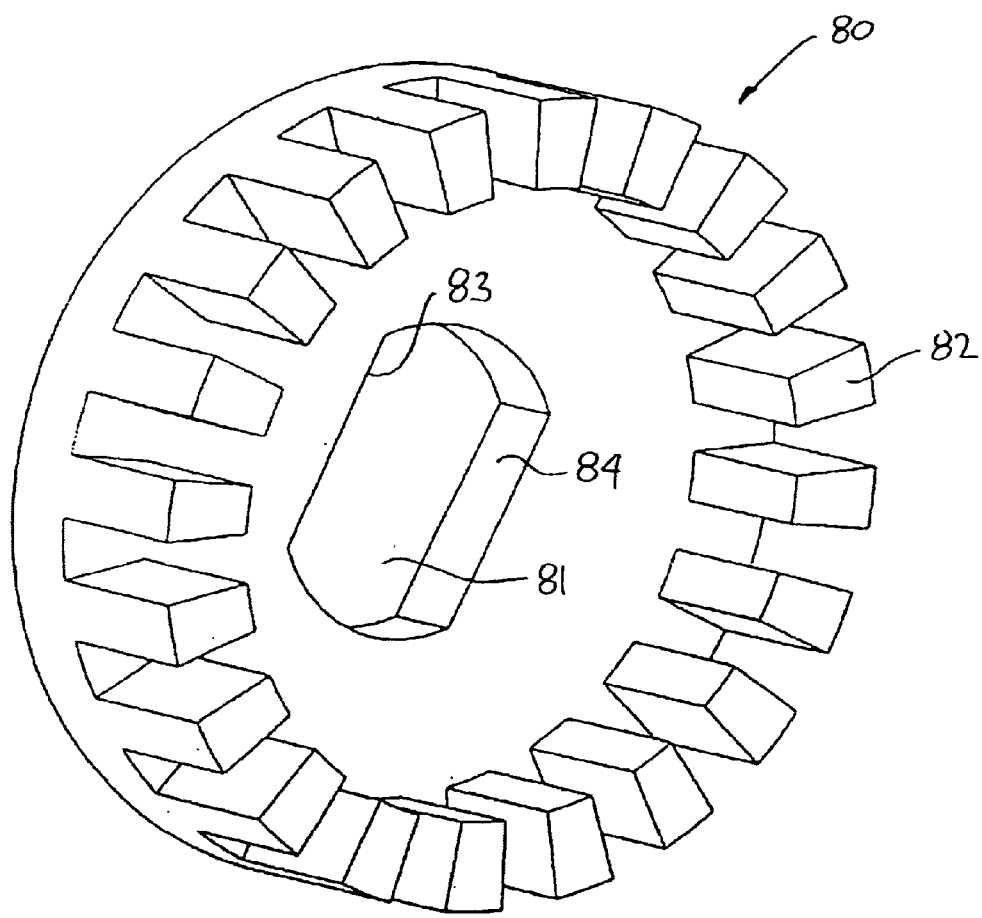
FIG. 9 shows a locking member.

The different members of the syringe and dose setting device shown in the drawings of FIGS. 1–3 have been described in detail with reference to these drawings, however, in order to provide an even better understanding of the present invention, some of the members are shown individually in, FIGS. 4–9, FIG. 4 showing the housing, FIG. 5 the dose setting member, FIG. 6 the piston drive member, FIG. 7 the coupling member, FIG. 8 the latch member and FIG. 9 the locking member. In all of FIGS. 4–9 the same reference numerals are used as in FIGS. 1–3 and broken lines are used to indicate structures hidden behind surfaces.

Next an embodiment according to the second aspect of the invention will be described with reference to FIG. 10 which in partial shows a pen-like syringe with a dose setting device, comprising a drive member 102 and a dose setting mechanism which simultaneously sets a given dose and stores the energy necessary for a subsequently driving the drive member in order to expel a dose of medicine from the syringe apparatus.

Figure 10:
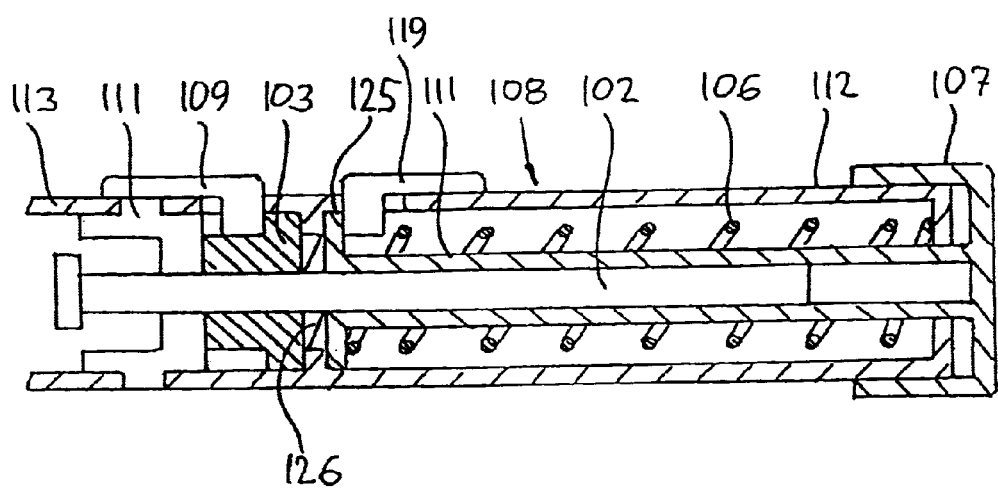
FIG. 10 shows in partial a cross section through a pen-shaped syringe comprising a dosing and expelling device according to a second embodiment of the invention.

The syringe is generally pen-like, being of elongate cylindrical form, with a pen body 108 closed at its left-hand end in FIG. 10 by a plunger guide 111 screwed into the pen body and having a cylindrical boss extending to the left and being externally threaded to accommodate a cartridge carrier 113 (shown in partial only). A cartridge of insulin (not shown) can be fitted into the cartridge carrier 113 before the cartridge carrier is screwed onto the boss on the plunger guide 111.

The guide 111 guides longitudinal movement of a drive plunger 102 progressively into the open end of the cartridge as insulin is injected through a needle (not shown) at the end of the carrier. The bore in the plunger guide has opposed flats for preventing rotation of the drive plunger 102 as it moves into the cartridge, the drive plunger having corresponding opposed flats.

Movement of the plunger 102 is achieved by energy stored in a helical spring 106, which is twisted as a pre-set dose of insulin to be injected is set by rotation of a cap 107 which can turn about a graduated sleeve 112 at the right-hand end of the pen body 108. The cap 107 has a window (not shown) through which graduations can be read to show the angle through which the cap has been turned.

The cap is integral with a drive sleeve 101 which can turn in a plain bearing defined by the sleeve 112 and has an annular ring 125 projecting at its left-hand end and formed with a ring of ratchet teeth. The spring 106 is secured, respectively, at its ends to a flange (not shown) at the left-hand end of the drive sleeve 101 and a flange (not shown) on the sleeve 112 so that, as the cap is turned, the spring is strained by being partially wound up.

The spring is a compression spring and both when strained torsionally and unstrained urges the teeth on the annular ring 125 of the drive sleeve into engagement with cooperating ratchet teeth 126 formed on a gear member 103. The arrangement of the ratchet teeth is such that the cap and drive sleeve can be turned in relation to the ratchet gear in one direction only with turning being accompanied by a series of clicks, as each successive ratchet tooth is engaged, i.e. an one-way ratchet mechanism. The ratchet gear member 103 is normally held against rotation by engagement of external teeth on the gear member 103 with internal teeth on a latch member 109. The latch member 109 has a leg which extend through slots in the housing to prevent rotation of the gear member in relation to the pen body, although the latch member can slide axially, as will be described later.

When the pre-set or "dialled up" dose of insulin is to be injected, the latch member 109 is slid axially to the left out of engagement with the ratchet gear member 103 so that the gear can rotate driven by the torque of the spring 106 through the drive sleeve and the ratchet teeth. Rotation continues until the cap has returned to its initial position defined by a positive stop between the cap and the pen body. The latch member is preferably biased towards its locked position by spring means (not shown).

The ratchet gear member 3 is internally threaded with a quick pitch thread to cooperate with a corresponding external thread on the stem of the drive plunger 102. Rotation of the ratchet gear and drive tapers is accompanied by axial movement of the plunger along the quick pitch thread since the plunger stem cannot turn in the plunger guide 111. Thus, the plunger is driven into the cartridge, expelling the pre-set dose of insulin. When the cap stops turning on the pen body, the plunger remains part-way along the inside of the cartridge.

According to the invention, a second latch or locking member 119 is provided which in its normal locked position slides on a rear surface of the annular ring 125 and thereby prevents the drive sleeve from moving rearwardly and thus to disengage from the gear member. However, if a dose is set too high a user may move the locking member to the right allowing the drive sleeve to be pulled backwards to thereby disengage the ratchet teeth from the gear member in which position it can be rotated backwardly to selectively adjust the set dose. As the drive sleeve is forced forwardly by the spring 106, it can only rotate when gripped and pulled backwardly by the user. When the dose has been adjusted the locking member is moved to its locked position (properly secured by any convenient means, either mechanically or by a spring means) and the syringe is ready to be released for expelling a set dose.

In an alternative embodiment no second latch member is provided, the ratchet gear members being held in engagement merely by spring means allowing the drive sleeve to be pulled backwardly and out of engagement by a user. Proper engagement between the ratchet members when not pulled apart to re-adjust the device is provided by spring means, either by the spring 106 alone or by an additional spring means. In order to protect against unintended disengagement the teeth of the ratchet members could be "under-cut" such that the drive member has to be rotated slightly forwardly as it is pulled rearwardly in order to disengage.

The procedure can be repeated until the cartridge is exhausted, after which the cartridge can be replaced by unscrewing the cartridge carrier 113 from the plunger guide 111.

While the present invention has been described in connection with the preferred embodiment shown in the various figures, it is to be understood that other similar embodiments may be used or modifications and additions may be made to the described embodiment for performing the same function of the present invention without deviating there from. For example, although the above disclosed coupling provides a preferred solution to desired dial up/dial down function, any coupling between the dose setting member and the coupling member allowing the dose setting member to be rotated in either direction, yet preventing the spring means to counter rotate the dose setting member could be used, this including a manually actuatable coupling such as described above with respect to FIG. 10. Further, in the shown embodiment most elements are arranged coaxially, however, this can be changed wherever specific needs make this convenient for the skilled person. When it is described that two elements are acting together, this may imply that they are directly or indirectly connected as long as the desired action is achieved.

Therefore, the present invention should not be limited to any single embodiment, but rather construed in accordance with the appended claims.

What is claimed is:

1. A dose setting device for use in combination with a fluid-filled reservoir, the dose setting device for repetitive injection of individual set doses of fluid from the reservoir, the dose setting device comprising:
    a housing;
    a drive member to expel a dose of fluid from the reservoir;
    a spring for driving the drive member to expel the dose;
        a dose setting assembly mounted in the housing and connected to the spring, the dose setting assembly comprising a first portion being moveable by a user in a first direction to set a selected dose against the bias of the spring and a remaining portion, wherein movement of the first portion is accompanied by a straining of the spring, and wherein the first portion is moveable in an opposite direction to selectively adjust the set dose without moving the drive member and wherein the first portion is in continuous engagement with the remaining portion of the dose setting assembly;
    a latch means associated with the housing to retain the apparatus in the set position against the bias of the spring; and
    wherein the latch means is releasable to cause the drive member to expel the set dose from the fluid-filled reservoir when the dose-setting device is used in combination therewith, the force for expelling the set dose being provided by the spring.

2. A dose setting device as defined in claim 1, wherein the dose setting assembly further comprises a coupling member in displaceable engagement with the dose setting member, the spring acting on the coupling member, the coupling member acting on the dose setting member.

3. A dose setting device as defined in claim 2, further comprising a threaded member with a first internal thread, the drive member being a longitudinal drive member having an external thread corresponding to the first internal thread, the threads being non-locking and having a pitch angle whereby axial movement of the drive member is obtained by an axial force applied to the drive member by the spring.

4. A dose setting device as defined in claim 2, wherein the dose setting member and the coupling member comprise mutually cooperating surfaces providing a coupling there between such that movement of the dose setting member in order to set a dose results in straining of the spring.

5. A dose setting device as defined in claim 4, wherein one of the dose setting member and the coupling member is rotationally mounted on the drive member, the other being arranged in sliding, non-rotational engagement with the drive member.

6. A dose setting device as defined in claim 5, wherein a coupling is arranged between the cooperating surfaces of the dose setting member and the coupling member, the coupling providing a resistance against rotation which is sufficient to prevent the spring from counter rotating the dose setting member, the resistance being easily overcome by a user rotating the dose setting member in either direction, whereby a user can selectively increase or decrease a dose setting.

7. A dose setting device as defined in claim 5, wherein the dose setting member is rotationally mounted on a threaded portion of the drive member whereby selectively setting a dose results in an axial movement of the dose setting member relative to the drive member, and the coupling member is arranged in sliding, non-rotational engagement with the drive member, the spring acting on the coupling member in a direction corresponding to the longitudinal axis of the drive member.

8. A dose setting device as defined in claim 7, wherein the threaded connection between the dose setting member and the drive member is of the non-locking type, and wherein a coupling between the dose setting member and the coupling member allows the dose setting member to be rotated in either direction, yet preventing the spring to counter rotate the dose setting member.

9. A dose setting device as defined in claim 1, further comprising a threaded member fixed in the housing and comprising a first internal thread, the drive member being a longitudinal piston drive member having an external thread corresponding to the first internal thread, the threads being non-locking having a pitch angle whereby axial movement of the piston drive member is obtained by an axial force applied to the piston drive member by the spring.

10. A dose setting device as defined in claim 9, wherein the dose setting member comprises a second internal thread, the dose setting member being rotationally mounted on the external thread of the piston drive member, whereby selectively setting a dose results in an axial movement of the dose setting member relative to the piston drive member.

11. A dose setting device as defined in claim 10, wherein the dose setting assembly further comprises a coupling member arranged in sliding, non-rotational engagement with the piston drive member, the spring acting on the coupling member in a direction corresponding to the longitudinal axis of the drive member, the coupling member acting on the dose setting member.

12. A dose setting device as defined in claim 11, wherein the dose setting member and the coupling member comprise mutually cooperating surfaces providing a coupling there between such that rotation of the dose setting member to set a dose results in straining of the spring as the coupling member is driven backwardly.

13. A dose setting device as defined in claim 12, wherein the threaded connection between the dose setting member and the piston drive member is of the non-locking type, and wherein the coupling between the dose setting member and the coupling member allows the dose setting member to be rotated in either direction, yet preventing the spring to counter rotate the dose setting member.

14. A dose setting device as defined in claim 12, wherein the coupling is arranged between the cooperating surfaces of the dose setting member and the coupling member, the coupling providing a resistance against rotation which is sufficient to prevent the spring to counter rotate the dose setting member, the resistance being easily overcome by a user rotating the dose setting member in either direction, whereby a user can selectively increase or decrease a dose setting.

15. A dose setting device as defined in claim 12, wherein the coupling between the dose setting member and the coupling member is provided by coupling parts having surfaces provided with sector shaped teeth having ramp shaped edges, the surfaces being forced against each other with the ramp shaped edges of the teeth on one surface abutting the ramp shaped edges of the teeth on the other surface, such that when the dose setting member is rotated in either direction, the teeth on the coupling parts will slide with their ramp shaped parts over each other, whereby the dosing member is axially displaced against the force of the spring and will jump back each time a top of the teeth is reached, the pitch of the toothing preferably being chosen so that a jump back takes place each time the dose setting is increased by a given dose unit.

16. A dose setting device as defined in claim 12, wherein the coupling is a frictional coupling provided between the cooperating surfaces, the necessary compression force between the surfaces being provided by the spring acting on the coupling member.

17. A dose setting device as defined in claim 12, wherein the coupling can be selectively engaged and disengaged allowing the dose setting member to be rotated in either direction.

18. A dose setting device as defined in claim 17, wherein the coupling is an one-way ratchet mechanism comprising first and second ratchet members and which can be disengaged by relative axial movement between the first and second ratchet members.

19. A dose setting device as defined in claim 1, wherein the latch means acts on the drive member.

20. A dose setting device for use in combination with a fluid-filled reservoir, the dose setting device for repetitive injection of individual set doses of fluid from the reservoir, the dose setting device comprising:
   a housing;
   a drive member to expel a dose of fluid from the reservoir;
   a spring for driving the drive member to expel the dose;
   a rotatable dose setting assembly mounted in the housing and connected to the spring, wherein the dose setting assembly comprises a coupling providing a resistance which is sufficient to prevent the spring to counter rotate the dose setting member, the resistance being easily overcome by a user setting the dose setting member in either direction, whereby a user can selectively increase or decrease a dose setting the dose setting assembly comprising a dose setting member coupled to the drive member, the dose setting member being moveable in a first direction from an initial position to a selected set position against the bias of the spring, wherein movement of the dose setting member is accompanied by straining of the spring,
   a first latch means associated with the housing to retain the device in a set position against the bias of the spring,
   the first latch means being releasable to cause the drive member to expel the set dose from the fluid-filled reservoir when the dose-setting device is used in combination therewith, the force for expelling the set dose being provided by the spring.

21. A dose setting device as defined in claim 20 comprising a second latch means associated with housing to retain the dose setting member in its coupled position, second latch means being releasable to allow the dose setting member to disengage from the driving means.

22. A dose setting device as defined in claim 20 wherein the spring is strained torsionally thus providing a rotating force on the dose setting member.

23. A method of infusing a flowable drug into a living subject is provided, comprising the steps of:
   providing an injection device for repetitive injection of individually set doses of a drug from a reservoir, the injection device comprising a housing, a reservoir containing a drug to be injected and having an outlet means therefore, a drive member to expel a dose of drug from the reservoir, a spring member for driving the drive member, a dose setting assembly mounted in the housing and connected to the spring, the dose setting assembly comprising a dose setting member being moveable in a first direction to a selected set position against the bias of the spring, wherein movement of the dose setting member is accompanied by straining of the spring and wherein the dose setting member is moveable in a second opposite direction to selectively adjust the set dose, the dose setting member being freely moveable in the opposite direction, a latch means associated with the housing to retain the injection device in the set position against the bias of the spring, and the latch means being releaseable to cause the drive member to expel the set dose from the reservoir, the force for expelling the set dose being provided by the spring, the method comprising the further steps of:
   establishing a flow connection between the subject and the outlet means;
   selecting a dose by operating the dose setting member, and
   releasing the latch means thereby causing the spring to drive the drive member to expel the set dose of the drug from the reservoir.

* * * * *